US006342537B1

(12) United States Patent
Thomsen et al.

(10) Patent No.: US 6,342,537 B1
(45) Date of Patent: *Jan. 29, 2002

(54) GEL FOR TREATMENT OF SKIN DISEASES AND FOR DISINFECTION OF THE SKIN

(75) Inventors: John Brown Thomsen, deceased, late of Gattieres (FR), Aase Brown Thomsen, legal representative; Jens C. Moller, Lemvig (DK)

(73) Assignee: John Brown Thomsen, Gattieres (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/416,940

(22) Filed: Oct. 13, 1999

Related U.S. Application Data

(63) Continuation-in-part of application No. 08/714,162, filed as application No. PCT/EP95/01025 on Mar. 20, 1995, now Pat. No. 5,981,605.

(30) Foreign Application Priority Data

Mar. 21, 1994 (DK) .............................................. 0325/94

(51) Int. Cl.$^7$ ........................ A61K 47/10; A61K 47/38; A61K 9/70
(52) U.S. Cl. ................. 514/724; 514/772.1; 514/772.5; 514/772.6; 514/781; 514/969
(58) Field of Search ............................ 514/724, 772.1, 514/772.5, 772.6, 781, 969, 970, 777

(56) References Cited

U.S. PATENT DOCUMENTS

| | | | |
|---|---|---|---|
| 3,016,328 A | | 1/1962 | Pepper et al. |
| 4,237,136 A | * | 12/1980 | Herrling ..................... 514/258 |
| 4,247,547 A | | 1/1981 | Marks |
| 4,431,633 A | * | 2/1984 | Machlowitz et al. ..... 424/209.1 |
| 4,590,214 A | | 5/1986 | Zamore |
| 4,593,048 A | | 6/1986 | Sato et al. |
| 4,671,955 A | | 6/1987 | Palinczar |
| 4,849,455 A | | 7/1989 | Eggers |
| 4,992,475 A | | 2/1991 | Marcel |
| 5,013,545 A | | 5/1991 | Blackman et al. |
| 5,098,717 A | | 3/1992 | Blackman |
| 5,145,663 A | | 9/1992 | Simmons |
| 5,288,486 A | | 2/1994 | White |
| 5,331,012 A | | 7/1994 | Riddick et al. |
| 5,376,366 A | | 12/1994 | Petchul et al. |
| 5,840,742 A | * | 11/1998 | Camden ..................... 514/383 |

FOREIGN PATENT DOCUMENTS

| | | |
|---|---|---|
| DE | 1000367 | 1/1957 |
| EP | 0 176 720 | 4/1986 |
| EP | 0 320 254 | 6/1989 |
| FR | 2613621 | 10/1988 |
| GB | 2 017 491 | 10/1979 |
| GB | 1 593 097 | 7/1981 |
| SE | 466 134 | 1/1992 |
| WO | 93/00114 | 1/1993 |

OTHER PUBLICATIONS

"A Surface Test for Virucidal Activity of Disinfectants: Preliminary Study with Herpes Virus", R. Tyler et al, Journal of Hospital Infection (1987) 9, 22–29.
"Quantitative Evaluation of the Effects of Disinfectants Against Viruses in Suspension Experiments", D. Moldenhauer, pp. 544–554 (1984).
"In Vitro Virucidal Activity by Components of a Topical Film–Forming Medication", B. Rodu et al, J. Oral Pathol 1988, 17:324–326.
Chem. Abstract, 90:76562r (1979).
D. Moldenhauer, "Quantitative Evaluation of the Effects of Disinfectants Against Viruses in Suspension Experiments" Sbl. Bakt. Hyg., I.A. bt. orig. B. vol. 179, pp. 544–554 (1984).
B. Rodu & F. Lakeman, "In vitro Virucidal Activity by Components of a Topical Film–forming Medication", J. Oral Pathol, pp. 324–326 (1988).
R. Tyler & G. Ayliffe, "A Surface Test for Virucidal Activity of Disinfectants", Journal of Hospital Infection, vol. 9, pp. 22–29 (1987).
H.E. Morton, "Alcohols" in Disinfection, Sterilization and Preservation, $2^{nd}$ Ed., pp. 301–318, 1997.
J.B. Thomsen, "Concentration/Formulation Experiments"—Declaration, Aug., 1998.
S. Mogensen, Blackman et al.—Declaration, Sep., 1998.
H. K. Andersen, In Vitro Antiviral—Declaration, Sep., 1998.
F.T. Black, Clinical Trial—Declaration, Sep., 1998.
Seelig and Gould, "Osmosis As an Important Factor in the Action of Antiseptics", manuscript presented to Western Surgical Association Dec. 10, 1910, pp. 262–270.
Harrington, "The Germicidal Action of Alcohol", Boston Medical and Surgical Journal (1903) pp. 548–552.
Christiansen, "Zur Theorie und Praxis der Alkoholdesinfektion", Aus dem Institut fur allgemeine Pathologie in Kopenhagen (1918) pp. 275–305.
"Microbiology: An Introduction", Fifth Edition, Tortora, Funke and Case, Benjamin Cummings Publishing Co. pp. 195–196 (1994).

* cited by examiner

Primary Examiner—William R. A. Jarvis
Assistant Examiner—Vickie Kim
(74) Attorney, Agent, or Firm—Burns, Doane, Swecker & Mathis, L.L.P.

(57) ABSTRACT

Gel for local treatment of skin diseases and for prophylaxis, characterized by containing more than 90% of a drying and/or protein coagulating, short-chained alcohol or alcohol mixture, primarily ethanol, and possibly adjuvants or additives and by containing a gelling agent, that possesses good skin-adhesive properties, that gives a matrix formation of alcohol or alcohol mixtures, that creates an evaporation inhibiting effect, gives a prolonged effect, and form a protective plaster when the gel has dried.

20 Claims, No Drawings

GEL FOR TREATMENT OF SKIN DISEASES AND FOR DISINFECTION OF THE SKIN

This application is a Continuation-in-Part of Ser. No. 08/714,162, filed Oct. 29, 1996 now U.S. Pat. No. 3,981,605, which is a S371 application is of PCT/EP95/01025 filed Mar. 20, 1995.

This application concerns a matrix-forming and skin-adhesive, anti-evaporant gel for local treatment of skin diseases, skin infections, for both curative and prophylactic treatment of wounds and treatment of insect bites and stings, in both humans and animals. More precisely, the invention relates to a gel characterized by containing lower alkanol in a concentration of more than 90% and by containing a gelling agent, such as ethyl(hydroxyethyl)cellulose, hydroxypropylcellulose or another suitable gelling agent, and possible additives, whereby the gel can be applied to the skin efficiently, easily, and without complications.

BACKGROUND

Infectious skin diseases, viral, microbial and parasitic, are widespread. Some examples of skin diseases are viral skin infections caused by, for example, Herpes simplex virus or Varicellae Zoster virus, bacterial skin infections caused by, for example, *Staphylococcus aureus*, fungal infections caused by, for example, *Trichophyton rubrum*, for eliminating skin parasites, such as *Sarcoptes scabiei* var. *hominis*. The virus infection caused by Herpes simplex, alone occurs with approximately 100 million new cases per year, and in the western world there are 250–400 million eruptions of herpes labialis per year.

Herpes simplex is caused by herpes virus (HSV). Herpes (HSV) simplex virus occurs in two different types, type 1 and type 2. Herpes on the lips and around the mouth (Herpes labialis) is usually caused by type 1; most incidences of Herpes on and around the genitals (Herpes genitalis) are caused by type 2.

The first infection with HSV (primary infection) varies symptomatologically. Usually it occurs during childhood. An this first Infection, HSV-DNA is incorporated as a latent virus into the cells. Intermittently, virus proliferation occurs, resulting in Herpes outbreaks (these outbreaks are called secondary infections). Most Herpes outbreaks in adults are secondary, where the infection flares up due to reduced resistance, febrile diseases (e.g. Pneumonia), traumas, or the effects of cold, heat., or light.

The outbreak starts with flushing, swelling, itching, and pain in the infected area followed by necrosis and a suppurative ulceration which is the most troublesome symptom. A spontaneous healing of the wounds will occur in approximately 10 to 14 days.

The outbreak of Herpes genitalis—mentioned above—is identical to that of Herpes labialis except for the fact that Herpes genitalis is located on and around the genitals.

The number of therapeutics for, for example, HSV skin infections is very limited, and the present antiviral chemotherapy has not convincingly been proved efficient. Furthermore, there exists a few products for advancing the healing of established HSV-wounds and inhibition of further outbreaks. However, none of these products have any convincing effect.

In U.S. Pat. No. 4,628,063 Haines et al disclose the antiviral activity of lidocaine against HSV. This activity is disclosed also by Yanagi, K., et al Arch. Virol. (1989) 10: 151–159. Haines et al is cited in U.S. Pat. No. 5,331,012 by Riddick et al, who use a lidocaine composition as an anaesthetic treatment of skin lesions, some of which may be herpectic in nature. Alcohol is used as a solvent in '012. The results of the examples in '012, at best, confirm the antiviral performance of lidocaine disclosed by '063. The examples do not allow any conclusions to be drawn regarding any antiviral properties of alcohol itself.

Other examples of skin disorders for which there are currently few or no adequate remedies include insect bites and stings.

Other examples of skin disorders for which there are currently few or no adequate remedies include insect bites and stings. The stings of hymenoptera (bees, wasps and ants) contain a variety of components and are biochemically and immunologically distinct between species. Direct toxic effects are mediated by mixtures of low-molecular-weight compounds such as serotonin, histamine, and acetylcholine and several kinins. Polypeptide toxins in honeybee venom include mellitin, which damages cell membranes; mast cell-degranulating protein, which causes histamine release; apamin, a neurotoxin; and adolapin, which has inflammatory action. Enzymes in venom include hyaluronidase, which allows the spread of other venom components, and phospholipases, which may be among the major venom allergens.

Uncomplicated stings cause immediate pain, a wheal-and-flare reaction, and local edema and swelling that subside in a few hours. Multiple stings can lead to vomiting, diarrhea, generalised edema, dyspnea, hypotension, and collapse. Rhabdomyolysis and intravascular hemolysis may cause renal failure. Death from the direct effects of venom has followed 300 to 500 honeybee stings.

Large local reactions that spread $\geq 10$ cm around the sting site over 24 to 48 hours are not uncommon. These reactions may resemble cellulitis but are caused by hypersensitivity rather than secondary infection. Such reactions tend to recur on subsequent exposure but seldom are accompanied by anaphylaxis and are not prevented by venom immunotherapy.

An estimated 0.4 to 4.0 percent of the US population exhibits clinical immediate-type hypersensitivity to insect stings, and 15 percent may have asymptomatic sensitization manifested by positive skin tests. Persons who experience severe allergic reactions are likely to have similar reactions after subsequent stings; occasionally, adults who have had mild reactions later experience serious reactions. Mild anaphylactic reactions from insect stings, as from other causes, consist of nausea, abdominal cramping, generalised urticaria, flushing and angioedema. Serious reactions, including upper airway edema, bronchospasm, hypotension, and shock, may be rapidly fatal. Severe reactions usually begin within 10 minutes of the sting and only rarely develop after 5 hours. Unusual complications, including serum sickness, vasculitis, neuritis, and encephalitis, develop several days or weeks after a sting.

From the literature it is known to use alcohol as disinfectant against, for example, virus including HSV—see, for example, R. Tyler; Journal of Hospital Infection (8: 22–29; 1987). The present inventors have found that when using alcohols as normal liquids (i.e. without taking steps to avoid evaporation) a poor and very brief effect is achieved due to the very rapid evaporation of the alcohols. Also the use of alcohols at concentrations below 90% by weight gives inadequate results.

Furthermore, Moldenhauer, in Zbl. Bakr. Hyg., I Abt. Orig. B 179, 544–554 (1984) compares surface disinfection properties of ethanol, isopropanol, formaldehyde and benzalkonium chloride by suspending virus suspension (including HSV, influenza, cocksackie-B and mumps) in those compounds or solutions. Alcohol concentrations above 90% were not tested. Furthermore in these two references alcohol is being used for surface disinfection properties and not for treatment of infections and the symptoms thereof.

In U.S. Pat. No. 5,145,663, a disinfectant, consisting of 65–75% isopropyl alcohol, 8–12% propylene glycol, and potential inert ingredients or disinfectants or antiseptics, is mentioned. The patent does not mention gels.

In GB-A-2017491 a gel containing alcohol is used as a hand-wash for bacterial disinfection.

In U.S. Pat. No. 5,288,486 viscosified alcohol compositions containing 30 to 90% alcohol are used to disinfect hands and sites of invasine medical procedures. The examples show antimicrobial activity and activity against the yeast *Candida albicans,* but not on skin infected with such microbes.

In the above references describing the use of alcohol, either as such or as a solvent for other active disinfectant agents, in surface disinfection of the skin, the alcohol will remain in contact with the skin for a relatively short period of time. The compositions, if they are washing compositions when they may contain a thickener such as sodium chloride, are generally rinsed off with water. Treatment with no-rinse compositions and alcohol wipes applies a relatively low amount of composition and the alcohol evaporates quickly. The alcohol is, in particular, not in contact with the skin long enough for penetration to layers below the stratum corneum (dermis and epidermis).

Ethanol has been used extensively in pharmaceutical compositions used for topical application to the skin. Compositions including a gelling agent have, likewise, been used for such application. However in none of these disclosures is the alcohol itself used as an agent for treating skin diseases. The following references are relevant.

In U.S. Pat. No. 3,016,328 and in U.S. Pat. No. 4,590,214 a mixture of a dialdehyde and an alcohol is mentioned. Without evaluating the effect, it can be established that none of these products include alcohol and gel-forming agents.

WO 93/00114 describes a method for reducing the duration of HSV-infection by applying a mixture of an anaesthetic and a surface-active ingredient with suitable antiviral activity. It does not mention gelling agents.

U.S. Pat. No. 4,247,547 mentions the use of gels containing alcohols and the dermatologically active tretinoin for treatment of acne. Tretinoin is a skin-irritant and the compositions would be wholly unsuitable for treatment of skin infected by HSV. Also the concentration of water in the compositions is unclear.

In Chemical Abstracts 90:76564r (1979) an antiseptic paste is disclosed containing about 80% by weight ethanol, 13% water and a thickener.

U.S. Pat. No. 5,013,545 describes a gel consisting of about 60 to about 90% ethanol, 0.5–30% water, and an active ingredient, such as an antihistamine. In the context of the disclosure, where rapid bactericidal and antiseptic performance is sought, the preferred range for the alcohol concentration is 60 to 80% values of more than 90% for the alcohol concentration are contraindicated by the cross-referenced text book by Morton, "Alcohols" in *Disinfection, Sterilisation and Preservation* 2nd ed. (1977) pp301 et seq. Morton discloses that (ungelled) compositions containing more than 90% alcohol have bactericidal performance which is too slow for the activity sought by '545. This patent does not mention activity on viral skin infections such as Herpes. Further, none of the worked examples teaches how to produce a stable gel with more than 80% alcohol.

U.S. Pat. No. 5,098,717 describes a gel based on 60–90% ethanol and as active ingredients an antihistamine and an antipruritic.

Carrier gels for pharmaceuticals based on ethanol and water are described in the patent literature, see, for example, SE 466134. In U.S. Pat. No. 4,593,048 it is mentioned that the penetration into the circulation by pharmaceuticals, dissolved in ethanol and applied topically, is accelerated when various adjuvants are used. The formulation contains surface-active ingredients as penetration aids for pharmaceuticals for percutaneous systematic administration. The compositions are not used to treat skin disorders.

An article by B. Rodu and F. Lakeman ("In vitro virucidal activity by component of a topical film-forming medication," J.Oral Pathology 17: 324326; 1988) mentions in vitro trials of a preparation consisting of approximately 80% ethanol, 7% tannic acid, 2.5% salicylic acid, and 1% boron acid. The tests were intended to evaluate the in vitro properties of the product Zilactin, which contains those ingredients and a hydroxy propylcellulose gelling agent. The in vivo performance of the gel against HSV has, however been found to be limited.

A specific antiviral preparation for topical treatment of Herpes is Zovir/Zovirax cream (Zovir is a registered trademark), which contains 5% aciclovir.

The United States Pharmacopeial Convention (1998) writes: Topical acyclovir is not effective in the treatment of recurrent herpes genitalia of herpes febrilis (labialis) infections in nonimmunocompromised patients, although topical acyclovir may cause some reduction in the duration of viral shedding. Also, there is no evidence that topical acyclovir will prevent the transmission of herpes infection to others or that it will prevent recurrent infections in the absence of signs and symptoms of infection. Further, (From Harrison's Principles of Internal Medicine, $14^{th}$ edition): Acyclovir-resistant strains of HSV are being identified with increasing frequency, especially in HIV-infected persons.

Acyclovir has been administered systemically for the treatment of Varicellae zoster virus. However reports have indicated that the treatment limited the immune response with consequent failure to develop resistance to the disease.

Surprisingly, it has now turned out that it is possible to produce an effective gel for treating skin diseases and for controlling skin parasites without using anti-histamines, anaesthetics, anti-inflammatory agents, and totally without using pharmaceuticals, including biocides against skin parasites.

Ethyl hydroxy ethylcellulose (EHEC) is produced by a first swelling native cellulose in alkali, then adding ethylene oxide to cellulose hydroxyl groups activated in the first step, then etherifying hydroxyl groups in the product by reacting them with ethyl chloride after alkali treatment. In the ethylene oxide treatment step ethoxy units may be added to the hydroxyl group on a pendant group derived from the earlier reaction of an ethylene oxide molecule with a cellulose-hydroxyl group. In the etherification step, hydroxyl groups of pendant groups and of cellulose-hydroxyl group may be reacted. The polymer product thus contains ethoxy 2-ethoxyethyleneoxy and ethoxypoly(ethyleneoxy) pendant groups. The reactions can be controlled so as to provide EHEC products with a variety of different degrees of substitution, and molar substitution (i.e. a measure of the average ethyleneoxy units per etherified group). These parameters, as well as the degree of polymerisation/molecular weight, affect the properties of the polymer in solution.

The performance of EHEC in aqueous systems, where it is used as a thickener and dispersing agent, for instance in paints and cement based mortar, has been studied (T örnquist, J, Farg och Lack Scandinavia, 31, 291–295 (1985), Carlsson, A et al polymer, 27, 431–436 (1986)).

OBJECTS OF THE INVENTION

One object of the invention is to provide a new method of treatment of insect bites and stings by application to the skin at the site of the said bite or sting of a composition comprising high concentration of alkanol.

Another object of the invention is to provide a new method of treatment of skin infected by herpes virus (Herpes simplex and Herpes varicellae-zoster virus) by application, usually repeated application, of a composition in which alkanol is present in high concentration and as essentially the sole anti-viral active ingredient.

Another object of the invention is to provide a new method of treatment of intracellular herpes simplex viral infection by application to the infected tissue of a composition in which alkanol is present in high concentration and as essentially the sole antiviral active ingredient.

Another object is to provide novel compositions comprising gelled $C_1$, $C_3$ and/or $C_4$ alkanols for treatment of skin disorders and the use of such compositions in methods of treating skin disorders.

SUMMARY OF THE INVENTION

A new gel-form pharmaceutical composition according to the invention comprises a liquid and a high molecular weight polymer gelling agent dissolved in the liquid, characterised in that the composition comprises more than 90% by weight based on the total weight of the composition of a lower alkanol which has up to four carbon atoms and less than 10% by weight water based on the total weight of the composition.

The composition optionally comprises one (or more) enhancing agent which enhances the effect (for instance the antiviral effect) of the alkanol composition. In one aspect of the invention, preferably the composition is substantially free of antihistamines, anaesthetics, anti-inflammatories, irritants and any immunogenic compounds or compounds which disturb the immune system. Consequently, in the invention, concentration and crystallization of medicaments (which is a potential problem with prior art compositions in which alcohol is held as a solvent vehicle for such active compounds) will not occur when the solvent evaporates. Consequently, local overdosing resulting in irritative inconveniences is totally avoided.

In the present specification it will be understood that the term akanol includes alkane-mono-ols, alkane-diols, alkane-tri-ols and other alkane-poly-ols. Two or more hydroxyl groups in a single molecule must be attached to different carbon atoms. The lower alkanol preferably contains up to 4, preferably up to 3 carbon atoms. It may be a glycol (an aliphatic diol in which the hydroxyl groups are attached to different, not necessarily adjacent, carbon atoms) or polyol but is preferably a mono hydroxy compound. It can be a mixture of such compounds. Most preferably it includes ethanol optionally in combination with other lower alkanols.

In a further aspect of the invention there is provided a novel composition comprising more than 90% by weight of an alkanol selected from isopropanol, n-propanol, mixtures of isopropanol and n-propanol, mixtures of propanol, selected from isopropanol, n-propanol and mixtures thereof, and ethanol in which the ratio of propanol to ethanol is in the range 10:1 to 1:10, a polymeric gelling agent in an amount in the range 0.1 to 10% by weight and less than 10% by weight water.

In a further aspect of the invention there is provided a novel composition comprising more than 90% by weight of an alkanol selected from $C_1$, $C_3$ and $C_4$ alkanols, mixtures thereof and mixtures thereof with ethanol wherein the ratio of ($C_1$, $C_3$ and/or $C_4$ alkanol): ethanol is in the range 1:10 to 10:1, a polymeric gelling agent in an amount in the range 0.1 to 10% by weight and less than 10% by weight water.

In a further aspect there is provided a novel composition comprising at least 70% by weight n-propanol, less than 30% by weight water and 0.1 to 10% by weight polymeric gelling agent.

In a further aspect there is provided a novel composition comprising at least 80% by weight of an alkanol selected from $C_3$ and $C_4$ alkane-mono-ols and mixtures thereof, 0.1 to 10% by weight of a polymeric gelling agent and less than 10% by weight water.

In all the above aspects it may be desirable to incorporate an effective denaturing amount of denaturant such as isopropanol or methanol as part of the alkanol mixture, where this is formed of other alkanols. Effective levels are in the range 1–10%. Other denaturants which may be included in the composition as part of non-alkanol component are diethylphthalate, e.g. in an amount of 0.1–2% by weight.

Thus, it has now surprisingly been found that a gel containing more than 90% ethanol or other lower alkanol is very effective for topical treatment of, for example, skin infections and skin parasites.

When using suitable gelling agents it is possible to transform a concentrated alkanol into a very suitable, effective, and stable gel. The invention is of particular value in the treatment of viral infections whose systems involve skin eruptions, especially herpes infections.

DETAILED DESCRIPTION OF THE INVENTION

Thus, the preparation of the invention consists of concentrated alkanol in such a form that it is usable as a topical preparation for immediate application to the diseased area of the skin including mucous membranes. While ethanol in lower concentrations, for example in concentrations of less than 60%, gives a distinct pain reaction, the use of the concentrated alcohol, for example in concentrations of more than 90% according to the invention, is almost painless even when it is used in open wounds. The preparation has a combined effect which is utilised optimally and over a prolonged period in the invention. Thus, an effective combination of drying the edematous tissue, coagulating proteins and destroying the pathogenic/agent, is achieved, and later, when it has dried, the gelling agent acts as a plaster protecting against infection and evaporation.

The gels of the invention create a matrix formation that prevents the alcohol from leaking out of the gel and flowing away from the site where the gel has been applied. At the same time the gel is gentle to the skin and easy to apply. It is possible, and preferred, for the composition to be transparent, and for the dried film of polymer gelling agent, remaining after the composition has dried on the skin, to be transparent to allow the underlying skin to be visible throughout treatment.

When the gel has dried it forms a protective film over a wound such as an HSV outbreak. Separately, all these activities contribute to avoid secondary bacterial infection. With the evaporation-limiting matrix formation the gel forms a barrier film on the surface between gel and air by means of which the evaporation of alcohol is drastically reduced. For a long time the alcohol in this way remains in contact with the skin by which means the ethanol has a possibility of diffusing into the skin and perform its effect in depth. Further, the plaster action of the gel prevents a rapid evaporation of the alcohol diffused into the tissue and, finally, after drying the plaster effect of the gel will offer protection against reinfection of the affected area. Thus, when choosing a gelling agent or a mixture of gelling agents, which form matrix with the ethanol and that form a film on the surface of the gel against the atmosphere, the extraordinary prolonged effect of the gel is achieved according to the invention.

The content of water is important to the effectiveness. The content should be less than 10%, preferably less than 5%, and optimally, in some cases, less than 1%. The amount of water should be below the equilibrium content of the composition under ambient conditions, that is under normal storage conditions at 20–24° C. and at 50–100% relative humidity, as well as at such humidity levels at temperatures up to body temperature (eg 37° C.). Thus the composition as a whole should, in effect be hygroscopic. The hygroscopicity is preferably due to the concentration of alkanol being higher than the concentration of alkanol in the presence of humid air. The equilibrium concentration of water in ethanol under these conditions is in the range 3 to 7% by weight of the sum of water and ethanol. The gelling agent may also contribute some hygroscopicity. If the content of water is too high the drying and antimicrobial effect and especially the antiviral effect is reduced which means that the effectiveness of the gel is reduced. Similarly, the concentration of alkanol is crucial to the effect on external skin parasites. It seems that the high concentration of alkanol may allow the alkanol to penetrate to layers of skin below the stratum corneum in therapeutic concentrations.

One of or a combination of several gelling agents which are usually soluble in the alkanol can be used. The gelling agent is a polymer, which may be linear, branched or cross-linked and may be naturally-derived, a derivative of such polymers, or may be wholly synthetic. The molecular weight is usually high, for instance at least $10^4$, preferably at least $5\times10^5$, and up to several million, for instance more than $10^6$. The polymer is preferably non-ionic in the composition. Suitable gelling agents include cellulose derivatives, especially cellulose ethers, such as alkyl- and hydroxyalkyl cellulose, for instance ethylcellulose, methylcellulose, hydroxyethyl cellulose, hydroxypropyl cellulose, especially ethyl(hydroxyethyl) cellulose (EHEC), carboxy methyl cellulose, other polysaccharides and derivatives, such as naturally derived polysaccharides and derivatives thereof, including modified carragenan; and synthetic polymers such as polyethylene glycols, polyethylene oxides, polyvinyl pyrrolidones and poly acrylic acid.

The cellulose derivatives which are useful in the invention usually have a high molecular weight, for instance more than $10^6$, although polymers with molecular weight from $10^5$ upwards may be useful. The degree of substitution/ derivatisation of cellulose ether derivatives useful in the invention is preferably relatively high, for instance higher than 1.0.

Particularly suitable cellulosic gelling agent for a highly concentrated ethanol are hydroxypropylcellulose (HPC), and ethyl(hydroxyethyl)cellulose (EHEC), EHEC is a derivative of cellulose with CA registration number 9004-58-4. EHEC is, as an example, sold under the trademark BERMOCOLL from Berol Kemi AB, such as BERMOCOLL OS. For example, an effectively gelling EHEC is achieved at degree of polymerisation of approximately 3,200, a degree of substitution of approximately 1.7 for ethylene (DS-ethyl=1.7) and of approximately 1.5 for hydroxyethyl (MS-hydroxyethyl=1.5). Cellulose ethers including EHEC are more precisely described in Kirk-Othmer, "Encyclopedia of Chemical Technology," 5:143, 1979(3. edition). See also "Faerg och Lack Scandinavia" 31:291–298;1985.

HPC is sold under the tradename KLUCEL™. KLUCEL hydroxypropylcellulose is a nonionic cellulose ether with a versatile combination of properties. It combines dual solubility in aqueous and polar organic solvents, thermoplasticity, and surface activity with thickening and stabilizing properties. Pharmaceutical grades of KLUCEL that meet the specifications of the European Pharmacopeia and, respectively, National Formulary are designated EP and NF.

Acrylic acid polymerics are also particularly suitable as gelling agent. Acrylic acid polymerics are, as an example, sold under the trademark Carbopol from BF Goodrich, such as Carbopol 940 and 941, Carbopol 940 NF and 941 NF, Carbopol 980 NF and 981 NF, or Carbopol 1342 and 1382. Those Carbopols are high molecular, non-linear polymerics of acrylic acid cross-linked with polyalkenyl polyether. Acrylic acid polymerics are more precisely described in "Kirk-Othmer, Encyclopedia of Chem.Tech," 20:216;1982 and in Ullmanns Encyclopedia of Ind.Chem," A21:752;1992.

Polyvinylpyrrolidones are a third example of a particularly suitable gelling agent. Polyvinylpyrrolidones, as an example, are sold under the trademark PVP K-30 and PVP K-90 from GAP. Polyvinylpyrrolidones are high molecular polymerics which are described in more detail in "Kirk-Otmer, Encyclopedia of Chem.Tech.," 23:963;1983 and in "Ullmanns Encyclopedia of Ind.Chem.," A21:143;1992 and others.

The gelling agents are used in amounts between 0.1% and 10%, depending on the choice of gelling agent or mixture of gelling agents, depending on the composition, the desired texture etc. The amount should preferably be sufficient to render the composition gel-like at room temperature and at normal body temperature so that it remains in place on the skin and does not spread or run off after application. The gel-like consistency, which is due to the viscoelastic properties of polymer solutions in solvents, depends upon molecular weight, degree of substitution as well as, for derivatives such as EHEC where the several units of derivatising agent may be added to each derivatised saccharide hydroxyl group, the molar substitution and type of substituent as well as the concentrations of polymer in the composition. The compositions should generally have high viscosity under low shear but, for optimal handling during manufacture and application, should be shear thinning. This combination of features can be achieved by appropriate selection of properties, as illustrated in the accompanying examples, for instance. For example, the viscosity-increasing effect of EHEC depends on the degree of polymerization and on the degree of substitution and, for the EHEC having a degree of polymerisation of 3200, mentioned above, a suitable concentration in ethanol is 0.5 to 2.0%, for instance around 1.0%.

This, for example, applies to pH-regulating agents such as bases, eg alkaline inorganic compounds or organic bases and mixtures by which some actions of alkanols are increased under certain circumstances. Inorganic bases which may be used include sodium and potassium hydroxide and carbamate. Organic bases include triethylamine, triethanol amine and other alkanolamines. For example, a content of 0.02% NaOH will increase the antiviral action of the ethanol. Thus in one embodiment of the invention the composition has a pH in the range 6 to 9.5, preferably an alkaline pH. Other additives that can be mentioned are the substances that form part of medicinal gels such as emollients, colorants, perfumes, menthol, camphor, w-protective agents etc. and the like by which the gel can be supplemented with further functional properties.

The composition should, however, be substantially free of pharmacologically active ingredients other than these optional enhancing agents.

The composition is preferably supplied in an air and moisture/moisture vapour-impermeable container. Such containers are, for instance, squeezable tubes, especially formed of metal foils or of plastics materials having moisture barrier properties. Such containers prevent compositions, whose water content is such that the composition is hygroscopic, from absorbing moisture from the atmosphere during storage and before use. By the use of such containers, therefore loss of drying activity of the gels is minimised.

According to the invention we have not only succeeded in producing a gel—with a concentrated content of alkanol—which is very effective and suitable for treatment of skin diseases, which is skin-adhesive and gentle to the skin, and which preferably does not contain other medicaments or pharmaceuticals. The mere omission of medicaments and pharmaceuticals such as antihistamines etc. has as a consequence that no adverse reactions or side-effects occur and that allergic reactions are completely eliminated. Further to this, as a consequence of the special mechanism of activity of alkanol, absolutely no resistance can develop among the responsible microorganisms or parasites. In choosing a gel with a matrix structure it is achieved that the alkanol, after application, does not accumulate in, for example, the nasolabial fissure at the angle of the mouth or in the groin but remains where applied. Further, as the gel shows pseudoplastic (viscoelastic) properties the gel is very easy to apply, and at the same time it regains its matrix structure and its structural firmness and exactly by that, as mentioned, remains on the site of application.

Because of the high concentration of alcohol the gel possesses other surprising properties. The skin-adhesive properties turn out to be very good, partially due to, the high content of alkanol, but also because of the choice of gelling agent, where especially EHEC, HPC, ASP, and PVP or combinations of these have lipophilic and hydrophilic properties giving the alcohol a very good contact with the skin.

The gelling agents, especially EHEC, HPC, ASP, and PVP or combinations of these, have hydrophobic-hydrophilic properties by which the release of alcohol towards the skin from the slow release matrix structure of the gel is adjustable. By doing this, it can be obtained that no release-inhibiting film is created between the alcohol-gel and the skin/mucous membranes. This, of course, is important for the continuous effect of the alcohol-gel on the site of application.

Thus, it is not necessary to add surfactants to achieve the correct contact between the skin and the gel as is the case in U.S. Pat. No. 4,593,048. The composition should generally be free of added surfactants.

Similarly, it is not necessary to add special binding agents nor to use plaster or tape in order to adhere the gel to the skin.

Gels according to the invention are physically and chemically stable for at least 12 months at 50° C. Among other things this is a result of the fact that addition of other active ingredients or adjuvants, which together with medicament or biocide may be labile during production and storage, is not needed. It is not necessary to add actual medicaments that, in turn, would require protective antioxidants etc. to secure the chemical stability of the very same medicaments during production and storage.

As the gel does not contain actual skin irritants it is, as mentioned, not necessary to add anti-irritants such as anti-histamines, anti-inflammatory agents or similar agents.

Because of the concentrated content of alcohol the gel is self-preserving. It is therefore not necessary to add antimicrobial preservatives against fungal growths nor products against bacteria or other micro-organisms, and it is not necessary to store the gel in refrigerator or the like. Omitting all these additives in the gel means that undesirable side-effects of such additives are eliminated.

Two very important properties are achieved in the invention by omitting surfactants, skin adhesives, pharmaceuticals, medicaments, antioxidants, antihistamines, or other anti-inflammatory agents, and because it is not necessary to add preservatives against fungi, bacteria, or other micro-organisms to the gel. First, in all simplicity, the gel is composed of non-allergenic substances. Secondly, owing to its special mode of action towards the infectious agents alkanol does not give rise to development of resistance. Furthermore the product does not disturb the hosts immune response.

For the sake of completeness it should be mentioned that many skin diseases, for example, Herpes simplex are complicated by secondary, usually bacterial infections. It is not necessary to add other pharmaceuticals to the gel to avoid secondary infections, as the alkanols in the gel with the long-term effect disinfects the area and protects it against reinfection via the plaster effect of the dried gel until the wound has healed.

Especially regarding Herpes infections the drying and protein coagulating effect is of great importance. The primary phases of the recurrent herpes outbreaks (secondary infections) are characterized by the formation of blisters, full of liquid. Apart from an immediate improvement of the itching and the pain reaction, a drying action on the oedema and blisters, that have already formed, is achieved when the preparation is applied at an early stage, and thus the blisters will disappear rapidly. If the herpes outbreak is not treated early enough the blisters will burst resulting in the formation of suppurating, open wounds that are characteristic of the later phases. When used during these phases, the preparation has an immediate drying effect by means of which the secretion ends, and the protein coagulating action destroy the superficial, necrotic cells.

The drying effect makes the product useful on moist skin areas. Here the drying effect has an immediate prophylactic action in relation to bacterial infections through a reduction of the growth conditions.

Similar advantages are seen when the gel is used to treat skin eruptions associated with other viral infections such as chickenpox. When applied to such skin eruptions the formation of blisters is prevented or they are dried and itching is minimised. The breaking of the skin with subsequent risk of infection is thus prevented.

In this connection we can also mention accidental skin injuries such as wounds and skin abrasions where the antimicrobial effect combined with the plaster action of the gel after drying has an indisputable preventive action in relation to wound infections.

The gel is further suitable for prophylactic treatment of physical skin injuries such as cuts, abrasions etc. This indication is not only based on the antimicrobial property of the preparation, but also on the protective effect of the dried gel having the "built-in" plaster effect that is achieved when the preparation has dried.

It is believed that use of the preparation in connection with treatment of burns will have a useful infectious prophylactic effect. Some eczematous diseases including allergic skin diseases are characterized by secondary infections. Here the invention will have great importance too, not least because of the non-allergenic property of the composition.

As mentioned above the gel is suitable for controlling externally parasitical and troublesome organisms. For example, the gel is suitable for external treatment of scabies, chigger and other ectoparasites.

A very effective preparation against skin infections and for eliminating external skin parasites can be obtained when using a gel in which the liquid consists of concentrated ethanol or a concentrated mixture of ethanol and other short-chained alkanols such as isopropanol or propylene glycol and containing in addition, additives such as drying and disinfecting agents, as well as the gelling agent, but no other ingredients.

The gel is also found to be useful for application to the site of inset bites and stings. The effect is thought to be due at least partially to the function of the concentrated alcohol in causing toxoid proteins in the sting to coagulate and be rendered inactive.

The invention is further illustrated in the following examples.

EXAMPLES

Examples of Compositions of the Gel (Examples 1 to 10)

Example 1

| Ingredient | Weight in % |
| --- | --- |
| Ethanol 99.9% | 91 |
| Water | 7 |
| Carbopol 980 NF | 2 |

Carbopol 980 NF (trade mark, BF Goodrich) has a molecular weight of around $7.5 \times 10^5$.

Example 2

| Ingredient | Weight in % |
| --- | --- |
| Ethanol 99.9% | 95 |
| Water | 3 |
| Carbopol 980 NF | 2 |
| Perfume | — |

Example 3

| Ingredient | Weight in % |
| --- | --- |
| Ethanol 99.9% | min. 99 |
| Carbopol 940 NF* | max. 1 |

*Carbopol 940 NF (registered trademark) an acrylic acid polymer from BF Goodrich

Example 4

| Ingredient | Weight in % |
| --- | --- |
| Ethanol 99.9% | 97.3 |
| Bermocoll OS* | 2.3 |
| NaOH or triethylamine | 0.1 |
| Water | 0.3 |

*Bermocoll OS (registered trademark) from Berol-Nobel = Ethyl (hydroxyethyl)cellulose

Example 5

| Ingredient | Weight in % |
| --- | --- |
| Ethanol 99.9% | 91.0 |
| EHEC* | 1.5 |
| Glycerine | 1.0 |
| Propyleneylycol | 3.0 |
| Water | 3.5 |

*(DP = 1,600, DS-ethyl = 0.8, MS-hydroxyethyl = 2.0)

Example 6

| Ingredient | Weight in % |
| --- | --- |
| Ethanol 99.9% | 91.0 |
| PVP K-30* | 2.5 |
| UV-absorbent | 1.0 |
| Camphor | 0–0.5 |
| Propylene glycol or adjuvant | 0–3.0 |
| Water | 0–2.0 |
| Polyvinyl alcohol | 0–1.0 |

*PVP K-30 (registered trademark) from GAF = Polyvinylpyrrolidone, average molecular weight of $4 \times 10^4$.

Example 7

| Ingredient | Weight in % |
| --- | --- |
| Ethanol | 91 |
| Carbopol 940 | 1 |
| PVP K-90 | 2 |
| Water | 4 |
| Surfactant | 2 |

Example 8

| Ingredient | Weight in % |
| --- | --- |
| Ethanol | 91.0 |
| Hydroxypropylcellulose | 2.5 |
| Xanthan gum | 0.1 |
| Isopropanol | 4.0 |
| Water | 2.4 |

The hydroxypropyl cellulose is selected for its solubility in the liquid. It is Klucel THF EP™.

Example 9

| Ingredient | Weight in % |
| --- | --- |
| Ethanol | 93.0 |
| Hydroxyethylcellulose | 1.0 |
| Ethylcellulose | 0.5 |
| Methylcellulose | 0.5 |
| NaOH | 0.02 |
| Water | 4.98 |

All the cellulose derivatives are selected for their solubility in the liquid.

Example 10

| Ingredient | Weight in % |
| --- | --- |
| Ethanol | 95.0 |
| Ethylhydroxyethylcellulose (Bermocoll OS) | 1.0 |
| Polyvinylpyrrilidone (MW 3.5 × $10^4$) | 2.2 |
| Polyethyleneglycol (MW 2 × $10^3$) | 0.2 |
| KOH | 0.02 |
| Water | 1.58 |

Examples of the use of the gels (Examples 11–18)

Example 11

Local Treatment of Herpes Simplex

When used for local treatment of Herpes simplex the effect depends on the time of application in relation to the start of the infection. Gels with particularly high concentration of alcohol are suitable, for example, gels mentioned in example 3, 4 or 10.

Within the first hours of the first phase which is characterized by itching, slight pain and prickling, followed by formation of vesicles, the gel is applied to the affected area approximately once an hour. The subjective symptoms dwindle immediately, and after 3–5 applications the outbreak is stopped and the vesicles disappear. After this, the gel is re-applied every 3–5 hours for 24 hours to secure that the outbreak has stopped completely.

Recent results seem to indicate that the subjective symptoms can be a good guiline for the application frequency, where the product is applicated when the subjective symptoms reappear.

When treatment is not started before the vesicles have burst and the gel is applied with a frequency of about every 3 hours the wounds are kept dry without the suppuration. The treatment is continued with decreasing application frequency until all wounds have started healing.

All three gels gave good results when used at these stages of the infection.

Example 12

Treatment of Herpes Zoster

When used for treating local skin outbreaks of Herpes zoster the gel mentioned in examples 2, 9 and 24 (see below) have been applied to the affected area. During the first 24 hours the gel is applied approximately every 2 hours, and after that at longer intervals as required. The vesicles heal up and the patient's inconveniences will abate rapidly.

Example 13

Treatment of Bacterial Skin Infections

The treatment of skin infections in connection with Acne vulgaris should be mentioned as an example of treating bacterial skin infections.

Gel in accordance with examples 1 and 6 according to the invention is applied to the infected skin areas. To begin with the gel is applied 3 times a day, and after that, when the infected areas have dried it is applied approximately once or twice a day. By means of this treatment with each of the gels rapid healing is achieved. A gel, in accordance with example 3, can be used in difficult cases directly on extensively infected areas.

Example 14

Treatment of Mycologic Skin Infections

The treatment of epidermophytosis (Tinea pedis) should be mentioned as an example of treating mycologically conditioned infections. Rapid healing of fissures, and successive cure of the fungus infection is achieved when a gel, in accordance with example 4, 7 and 8, is applied twice a day primarily, and after a few days only once a day.

Example 15

Control of External Parasites

As required a thin or thick layer of a gel, in accordance with example 3 and 9 of the invention, is applied to the infected area with the external parasites such as lice, scab mites, ticks and crab lice. In a short time the parasites are eliminated.

Because of the antimicrobial property of the gel, secondary infections after bites also heal up rapidly.

Example 16

Prophylacticum Against Skin Infections

The treatment of banal scraping wounds should be mentioned as an example of using the gel as a prophylacticum. Primarily the wound is cleansed with water/soap following classic principles. After that, gel is applied, for example, the gel mentioned in example 1. During the first 24 hours the gel is applied 3 times. After that, the gel is applied once a day until the wounds start to heal. Due to the properties of the dried gel, acting as an elastic, fixed plaster on the wound, a good protection of the wounds is achieved in between the applications.

Example 17

Treatment of Chickenpox (Variola)

The gel of example 4 is applied directly onto the individual eruptions on the skin of a patient with chickenpox as soon as possible after the eruption and every 2 to 4 hours thereafter. This immediately soothes the skin, reduces itching, prevents blister formation and renders the patient non-contagious in a shorter period of time. The gels of examples 3 and 10 have similar activity.

Example 18

Bee Sting and Other Insect Bite Treatment

The gel of example 4 is applied direct to the skin at the site of a bee sting as soon as possible after occurrence of the sting. The discomfort and swelling were immediately reduced and itching does not develop. This activity is thought to be due to an effect of the concentrated alcohol in coagulating protein in the insect venom injected into the skin. The gels of examples 3 and 10 have similar performance.

Further Examples

Example 19

98% by weight isopropyl alcohol (99.9%) and 2% by weight hydroxypropylcellulose (Klucel-HF EP) are mixed and stirred until a gel is formed. The composition when applied to bacterial skin infections and to insect bites has been found to have equivalent results to those of Examples 13 and 18.

Example 20

97% by weight isopropyl alcohol (99.9%), 1.1% by weight lidocaine and 1.9% by weight hydroxypropylcellulose (as used in Example 19) would be mixed and stirred until a gel is formed.

Example 21

49% by weight isopropyl alcohol (99.9%), 49.2% by weight n-propyl alcohol (99.9%) and 1.8% by weight hydroxypropylcellulose (as used in Example 19) would be mixed and stirred until a gel is formed.

Example 22

21% by weight isopropyl alcohol (99.9%), 77.2% by weight ethanol (99.9%) and 1.8% by weight hydroxypropylcellulose (same grade as used in Example 19) would be mixed and stirred until a gel is formed.

Example 23

This example indicates the importance of using ethanol in a concentration of more than 90% by weight to achieve efficacy in the treatment of herpes labialis eruptions. The ethanol was contacted with the skin using various different techniques described below.

23.1—No Prolonged Contact

The treatments were started at different phases in the progress of the eruptions (prodromal phase, vesicular phase with intact vesicles, and ulceration phase). Liquid ethanol and ethanol/water mixtures (as specified/in the following tables) were kept in air- and moisture-tight containers and opened immediately before the respective applications. The liquids were impregnated into cotton (cottonwool) balls and contacted with the skin at the site of the eruption though not kept in contact for an extended period of time. The application frequency was the same for each concentration within each test phase. The application frequency, however differed depending on the phase at which treatment commenced. The frequency for treatment commenced in the prodromal phase was once every ½ hour. The frequency was lowest for treatment commenced in the ulceration phase (3 or 4 times daily). The frequency for the intermediate phase was between those two figures.

TABLE 1

Treatment started at first symptom.
(Symptom relief, eruption abortion and pain refer to scores in the early phase)

| Ethanol Concentration | Symptom Relief | Eruption Abortion | Eruption Time Shortening | Pain |
|---|---|---|---|---|
| 60% | – | – | – | (–) |
| 85% | – | – | – | (–) |
| 90% | (+) | – | (+) | (+) |
| 95% | + | – | + | (–) |
| 99% | ++ | – | + | (–) |

TABLE 2

Treatment started in eruption phase
(Symptom relief, eruption abortion and pain refer to scores in the eruption phase)

| Ethanol Concentration | Symptom Relief | Eruption Abortion | Eruption Time Shortening | Pain |
|---|---|---|---|---|
| 60% | – | – | – | (+) |
| 85% | – | – | – | (+) |
| 90% | (+) | – | (+) | (+) |
| 95% | + | – | + | (+) |
| 99% | ++ | – | + | (+) |

TABLE 3

Treatment started in ulceration phase

| Ethanol Concentration | Symptom Relief | Eruption Abortion | Eruption Time Shortening | Pain |
|---|---|---|---|---|
| 60% | – | – | – | +++ |
| 85% | – | – | – | +++ |
| 90% | (+) | – | (+) | ++ |
| 95% | + | – | + | (+) |
| 99% | +(+) | – | + | (+) |

The results show that symptom relief was obtained in all phases with concentrations from 90% and above. When applied from first symptoms and from vesicular phase (without disrupted vesicles) some symptom relief was obtained in relation to itching and slight pain. When applied in the ulceration phase the symptom relief was related to some drying effect on the disrupted vesicles.

In none of the cases were abortions of eruptions obtained. The eruption times were slightly shortened. This was most likely for all phases due to the cleansing effect avoiding bacterial infections and for the ulceration phase the coagulating effect in relation to dead cells and thereby a further prophylactic effect against bacterial contamination.

23.2 —Prolonged Contact with Impregnated Cotton

Similar tests were carried out to those in Example 23.1 but keeping the impregnated cotton in contact with the skin for several minutes at each application, and re-impregnated 3 or 4 times per application period. The results are shown in Tables 4 to 6 below.

TABLE 4

Treatment started at first symptom.
(Symptom relief, eruption abortion and pain
refer to scores in the early phase)

| Ethanol Concentration | Symptom Relief | Eruption Abortion | Eruption Time Shortening | Pain |
|---|---|---|---|---|
| 60% | – | – | – | (+) |
| 85% | – | – | – | (+) |
| 90% | (+) | – | (+) | (+) |
| 95% | ++ | + | + | (+) |
| 99% | +++ | +(+) | + | (+) |

TABLE 5

Treatment started in eruption phase.
(Symptom relief, eruption abortion and pain
refer to scores in the eruption base)

| Ethanol Concentration | Symptom Relief | Eruption Abortion | Eruption Time Shortening | Pain |
|---|---|---|---|---|
| 60% | – | – | – | (+) |
| 85% | – | – | – | (+) |
| 90% | (+) | – | (+) | (+) |
| 95% | ++ | – | (+) | (+) |
| 99% | +++ | + | + | (+) |

TABLE 6

Treatment started in ulceration phase

| Ethanol Concentration | Symptom Relief | Eruption Abortion | Eruption Time Shortening | Pain |
|---|---|---|---|---|
| 60% | – | – | – | +++ |
| 85% | – | – | – | +++ |
| 90% | (+) | – | – | ++ |
| 95% | + | – | – | (+) |
| 99% | + | – | + | (+) |

Apart from a palliative effect on symptom relief with high concentrations (especially 95% and 99% ethanol) and some shortening of eruption time this intensive depot treatment had some abortive effect with the highest concentration (99%) in the early phase and in the vesicular phase. There was some variation in the treatment results. These variations are believed to be due to the difficulty in standardizing this application method. The results were greatly influenced by the pressure applied to the cotton ball during application. Too high a pressure prohibited ethanol from having contact to the skin or mucous membrane as the ethanol in the compressed part of the cotton closest to the skin was pressed away from the contact with the eruption. It is further believed that too high a pressure on the skin tissue compromises the tissues ability to absorb the liquid. Too light a pressure did not allow sufficient contact.

23.3—Prolonged Content with Alcohol in Glass Container

Similar tests to those conducted in Examples 23.1 and 23.2 were conducted but ethanol and ethanol/water mixtures were applied from a glass container by holding the opening of the container against the skin so as to allow the body of liquid in the container to contact the skin for several minutes. The results are shown in Tables 7–9.

TABLE 7

Treatment started at first symptom.
(Symptom relief, eruption abortion and pain
refer to scores in the early phase).

| Ethanol Concentration | Symptom Relief | Eruption Abortion | Eruption Time Shortening | Pain |
|---|---|---|---|---|
| 60% | (+) | – | – | (+) |
| 90% | + | – | (+) | (+) |
| 95% | ++(+) | ++ | ++ | (+) |
| 99% | +++ | ++(+) | ++(+) | (+) |

TABLE 8

Treatment started in eruption phase.
(Symptom relief, eruption abortion and pain
refer to scores in the eruption phase).

| Ethanol Concentration | Symptom Relief | Eruption Abortion | Eruption Time Shortening | Pain |
|---|---|---|---|---|
| 60% | (+) | – | – | (+) |
| 90% | + | – | (+) | (+) |
| 95% | ++(+) | +(+) | + | (+) |
| 99% | +++ | ++ | ++ | (+) |

TABLE 9

Treatment started in ulceration phase

| Ethanol Concentration | Symptom Relief | Eruption Abortion | Eruption Time Shortening | Pain |
|---|---|---|---|---|
| 60% | – | – | – | +++ |
| 90% | (+) | – | (+) | ++ |
| 95% | +(+) | – | (+) | (+) |
| 99% | +(+) | – | (+) | (+) |

A very strong symptom relief was obtained with 95% and 99% ethanol in the two early phases. Further an eruption abortive effect was clearly observed both with 99% and 95% ethanol. An eruption shortening effect was likewise observed with the same concentrations.

Though efficacious in many respects this "direct from bottle method" was difficult to apply and could only routinely be used for very small eruptions.

23.4—Application of Gelled Alcohol

In previous tests it has been shown that there is no difference in clinical activity between hydroxypropylcellulose (HPC) (of the grade used in Example 19) and ethylhydroxyethylcellulose (EHEC) (of the grade used in Example 5). In this example some of the gelled compositions contained 1.6% by weight HPC and others contained 1.6% by weight EHEC. The gelled ethanol (99.9%) or ethanol (99.9%)/water mixture was applied to the eruption area in a thick layer (not smeared) and left on the skin. The application frequency was the same as in Examples 23.1 to 23.3. The results are shown in Tables 10 to 12.

TABLE 10

Treatment started at first symptom.
(Symptom relief, eruption abortion and pain refer to scores in the early phase).

| Ethanol Concentration | Symptom Relief | Eruption Abortion | Eruption Time Shortening | Pain |
|---|---|---|---|---|
| 60% | (+) | − | − | (+) |
| 90% | + | − | (+) | (+) |
| 95% | +++ | +++ | +++ | (+) |
| 99% | +++ | +++ | +++ | (+) |

TABLE 11

Treatment started in eruption phase.
(Symptom relief, eruption abortion and pain refer to scores in the eruption phase).

| Ethanol Concentration | Symptom Relief | Eruption Abortion | Eruption Time Shortening | Pain |
|---|---|---|---|---|
| 60% | (+) | − | − | (+) |
| 90% | + | − | (+) | (+) |
| 95% | +++ | ++ | ++ | (+) |
| 99% | +++ | ++(+) | +++ | (+) |

TABLE 12

Treatment started in ulceration phase

| Ethanol Concentration | Symptom Relief | Eruption Abortion | Eruption Time Shortening | Pain |
|---|---|---|---|---|
| 60% | (+) | − | − | +++ |
| 90% | ++ | − | (+) | ++ |
| 95% | +++ | − | (+) | (+) |
| 99% | +++ | − | (+) | (+) |

The gelled alcohol compositions dried forming a clear "plaster" over the eruption.

The obtained symptom relief was here due to two factors. One of them was related directly to ethanol while the other was related to the dried gel. The dried gel, forming a plaster over the eruption felt very pleasant to the patient. It "sealed" the eruption site and in this way probably inhibited some evaporation of the absorbed ethanol. This "plaster-effect" was important in the first phases of the eruption and had a special effect in the ulceration phase where the wounds were closed with this gel-plaster.

The abortive effect was very pronounced especially for concentration of 95% and 99% ethanol during the two first eruption phases (prodromal phase and vesicular phase) and there was a significant shortening of the eruption times in total.

Side Effects and Adverse Reactions (All of Examples 23.1–4)

Pain was the only side effect observed. The last column in all tables indicates the pain reaction in connection with the application. In the early treatment phases, without ulceration, all concentrations only gave rise to some slight pain sensation. In the ulceration phase the pain reaction was very pronounced for the lower ethanol concentrations. 90% ethanol in the ulceration phase gave less pain or shorter duration while the 95% and 99% only gave rise to a slight pain of short duration.

The slight pain sensation observed during the non-ulceration phases was for the higher concentrations (above 90%) of very short duration (approximately 10 seconds) and characterised more as a smart or sting. I believe the observed diminished pain reaction to be due to a local anaesthetic effect of ethanol in these concentrations and that this local anaesthetic effect is one of the main causes for the observed symptom relief.

In conclusion it has been found that simple application of ethanol (tables 1, 2) have some general palliative effects of rather short duration. Only special, very intensive and prolonged application methods lead to a desired effect of shortening eruption time and especially to abortion of eruptions. It has been found that a gelled ethanol undoubtedly has a special performance, and is at the same time easy to administer and easy to standardise for patient treatment.

The final goal, the abortive effect, is probably the best indication of an in vivo antiviral activity. It can only be obtained with the special sustained application. For very small eruptions it can be obtained with the "closed chamber" direct application method (tables 7, 8), but the efficacious method for all eruptions is the use of a gelled ethanol (tables 10, 11).

Example 24

A pilot scale quantity of gel was formed by mixing 1000 ml ethanol (99.9% Pharmacopeia EU) and 16 g hydroxypropylcellulose (Klucel HF EP). The gel was kept in an air- and moisture vapour-tight aluminium tubes prior to use.

A controlled open trial in immunocompetent and otherwise healthy patients has been conducted, using the duration of untreated episodes in the same patients as controls. The trial was conducted in accordance with the European Union, GCP rules.

Patients

The patients were recruited through advertisements in the clinics of the University Hospital. The inclusion criteria were: Eighteen years old or above, immunocompetent, at least two recurrences of herpes labialis per year and culture proven HSV infection. The patients were asked to come to the hospital at the first recurrence, before starting any treatment. A detailed history was taken, especially concerning the duration of earlier untreated episodes. They were then informed about the trial. A written consent was obtained and a swab was taken, after disrupting the skin barrier and sent for HSV culturing and typing.

If culture positive, patients were instructed to treat the next recurrence as early as possible by applicating the gel every half hour for six hours and then four times a day for four days in all. Information on development of lesion, time to complete healing, (defined as intact skin with or without discolouration) and number of applications of gel were to be recorded in a patient diary together with possible side effects. After completing the diary the patients were seen again in the clinic and the information in the diary scrutinized jointly with the patient.

The description of the herpes labialis lesion was divided into six stages:

1. Prodromes without clinical signs.
2. Erythema with papule but without vesicles.
3. Erythema with intact vesicles.
4. Like 3 but with disrupted vesicles.
5. Crust formation.
6. Complete healing.

Forty-two patents were included. Within the planned trial period 20 patients have returned with the test tube and a patient diary after completing a course of treatment. There were 16 female and 4 male patients. The age ranged from 21 to 61 years (median 32). All of the 20 patients experienced typical prodromes before herpes labialis episodes, and were never in doubt about when a recurrence was going to start. Most of the 20 patients gave the time to complete healing of untreated recurrences as an interval. To minimize a possible "recall bias" we have only used the lowest values for comparison. The recalled duration of recurrent herpes labialis episodes varied from 6 to 14 days, median 10 days.

Statistics

Because of the relatively small number of patients evaluated, especially in the subgroups, the Wilcoxon matched-pairs signed-ranks test was used to see whether the duration of recurrent episodes treated with concentrated ethanol in a gel formulation differed from the duration of untreated episodes as recalled by the patients. Comparable results were obtained when the paired t-test was applied, data not shown.

All of the 20 HSV isolates were type 1. Five patients started treatment in stage 1, eight in stage 2 and seven in stage 3. The averaged results are shown in Table 13 below. Only one patient reported no benefit at all. The median time to complete healing in untreated recurrences as recalled by the patients was 10 days compared with 4.5 days for treated episodes which is highly significant p<0.001. If the results for the three groups of patients are looked upon separately the benefit for patients in stages 2 and 3 is significant. Reduction in median time to complete healing was 5.5 days (55%) and 4 days (40%) respectively with p values<0.02 for both stages. Only 5 patients started treatment in stage 1 and the differences all had a positive sign, but the group is too small for statistical analysis. In three patients treated in stage 1, three in stage 2 and on in stage 3, the recurrence of herpes labialis aborted during treatment i.e. the skin remained intact with ulceration.

TABLE 13

Reduction in time to complete healing

| Stage of eruption | Number of patients | Reduction in days[1] | p values[2] |
|---|---|---|---|
| All | 20 | 5.5 (55%) | <0.001 |
| Stage 1 | 5 | 10 (100%) | N.D.[3] |
| Stage 2 | 8 | 5.5 (55%) | <0.02 |
| Stage 3 | 7 | 4 (40%) | <0.02 |
| Stage 2 + 3 | 15 | 5 (50%) | <0.001 |

[1] Median
[2] Wilcoxon's signed-ranks test
[3] The group is too small for statistical analysis.

When patients in stage 1 (prodromes alone) are excluded to evaluate the efficacy of treatment in "late stages" (stages 2+3), the difference between untreated and treated recurrences was 5 days (50%) which is highly significant p<0.001.

The good compliance was illustrated by the actual number of applications 20 compared with the estimated 24 for a full course of treatment.

All the patients expressed appreciation of the local anaesthetic effect of the gel and the lack of cosmetic disturbance due to the transparency of the gel and the residual thin film.

Toxicity

The treatment was very well tolerated. Most of the patients in the later stages of herpes labialis experienced a light to moderate smart or sting of very short duration (10 to 20 seconds) immediately after application of the gel. No other side effects were reported.

Comments and Discussion

The topical treatment of recurrent herpes labialis with gelated concentrated ethanol as described here is by far the most efficacious reported up to now. The results of this trial showed an overall reduction of time to complete healing of 5.5 days, (4.5 versus 10 days), which is highly significant. The efficacy was demonstrated for all stages from the prodromal to the vesicle stage. When only late treatments, defined as papular or vesicle stages, are evaluated, the reduction in time is 5 days, (5 versus 10 days) which is also highly significant (p<0.001). Acyclovir has been the only available topical or oral antiviral treatment since the beginning of the eighties, but the published clinical data have been conflicting[1-4] but there seems to be a trend towards a limited effect when treatment is started early in the prodromal or erythema stages[5,6]. Recently n-Docosanol 10% cream in a placebo controlled study including 65 patients has been shown to shorten the mean healing time by approximately 3 days when applied (for up to a maximum of 10 days) in the prodromal or erythema stages, whereas no significant effect was seen in later stages. When all treatment cohorts were combined the reduction in time was 1.6 days which is still significant[7]. Topical 1% penciclovir cream applicated every 2 hours while awake for 4 days has also been reported to excerpt some effect on recurrent herpes labialis. In a placebo controlled multicenter trial including 1573 patients the reduction of time to loss of crusts (time to complete healing not given) was 0.7 days in early as well as late treatment groups which is statistically significant[8]. Both of these two last mentioned compounds are thus significantly less efficacious than gelated concentrated ethanol, and this accounts for overall results, early treatment and especially late treatment of recurrent herpes labialis.

The treatment was very well tolerated, the only reported side effect was a light smart or sting of very short duration in relation to the application of the gel in late stages. None of the patients had to stop treatment because of side effects. The compliance was excellent. The patients appreciated the minimal cosmetic disturbance caused by the gel, compared to cream, mainly due to the transparency of the gel and the residual thin film. The results of the present trial has confirmed the high efficacy and tolerability of gelated concentrated ethanol as a topical treatment of recurrent herpes labialis in early as well as later stages of the eruptions.

REFERENCE

1) Shaw M, King, Best J M, Banatvala J E, Gibson J R and Klaber M R. Failure of acyclovir cream in treatment of recurrent herpes labialis. BMJ 1985; 291:7–9 labialis. J. Infect. Dis. 1997; 176:78–83.

2) Spruance S L, Schmipper L E, Overall Jr J C et al. Treatment of Herpes simplex labialis with topical acyclovir in polyethylene glucol. J. Infect. Dis. 1982;146-85–90.

3) Whitley R J and Gnann J W. Acyclovir: A decade later.N.Engl.J.Med. 1992;327:782–789.

4) Fiddian A P, Yeo J M, Stubbings R and Dean D. Successful treatment of herpes labialis with topical acyclovir. BMJ 1983;286:1699–1701.

5) Rabborn G B, McGaw W T, Grace M and Percy J. Treatment of herpes labialis with acyclovir. Am.J.Med. 1988;85: suppl. 2A:39–42.

6) Whitley R J and Darby G. Anti-herpesvirus agents in: Reviews in contemporary pharmacatherapy. Marius Press. 1996;7:92–92.

7) Habbema L, De Boulle K, Roders G A and Katz D H. N-Docosanol 10% cream in the treatment of recurrent herpes labialis. Acta. Derm. Venereol 1996;76:479–481.

8) Spruance S L, Rea T L, Thorning C, Tucker R, Saltzman R and Boon R. Penciclovir cream for the treatment of Herpes simplex labialis. JAMA 1997;277:1374–1379.

Example 25

Inactivation of Herpes Simplex Virus with Ethanol, Methanol, Propanol, Isopropanol and Butanol Introduction Ethanol is an accepted disinfectant for viruses with an envelope. The purpose of this study was to measure the inactivating effect of "short-chained alcohols" on virus-infected cells.

Design

Four 96 well plates with confluent MRC-5 cell were infected with herpes simplex virus (HSV) type 1. After appearance of 50% cytopathic effect (CPE), the culture medium was removed, and rows of 12 wells were treated with 25 μl/well of the alcohols or buffer after the following scheme: The first row with undiluted, and the following with 96%, 90%, 80%, 70%, 60% and 50% alcohol, respectively—all dilutions performed in buffer (PBS). To the last row was added buffer. After 2, 4, 8, 16 and 32 min, respectively, two wells in each row were emptied and the cells overlaid with PBS. The plate was then frozen at —80° C. Afterwards the wells were seeded with a detection layer of MRC-5 cells and the plates were placed at 37° C. for 44 hours. Virus surviving the treatment with alcohol was detected by the appearance of CPE, characteristic for HSV in the detection monolayer.

Results

All of the alcohols had a disinfecting effect on HSV as seen from Tables 14. Use of undiluted and the highest concentrations of the alcohols were most effective, but also lower concentration were effective. A time-related effect was not seen in this study, for any of the alcohols. For comparison of the four alcohols and ethanol, the disinfecting effect has been calculated by counting the number of virus-free wells in each row as seen in table 15.

TABLE 14

Reading of HSV - CPE after 44 hours with the detecting cell-layer.

| Alcohol | | 2 | | 4 | | 8 | | 16 | | 32 | |
|---|---|---|---|---|---|---|---|---|---|---|---|
| Methanol | Undiluted | 0 | 0 | 0 | 0 | 0 | 0 | 0 | 0 | 0 | 0 |
| | 96% | 0 | 0 | 0 | 0 | 0 | 0 | 0 | 1 | 1 | 0 |
| | 90% | 0 | 0 | 0 | 0 | 0 | 1 | 1 | 1 | 1 | 0 |
| | 80% | 1 | 1 | 0 | 0 | 1 | 1 | 0 | 1 | 1 | 0 |
| | 70% | 1 | 1 | 1 | 1 | 1 | 1 | 1 | 1 | 0 | 1 |
| | 60% | 1 | 1 | 0 | 1 | 1 | 1 | 0 | 1 | 1 | 1 |
| | 50% | 1 | 0 | 1 | 1 | 1 | 2 | 2 | 2 | 1 | 1 |
| | Untreated | 3 | 3 | 3 | 3 | 3 | 3 | 3 | 3 | 3 | 3 |
| Propanol | Undiluted | 0 | 0 | 0 | 0 | 0 | 0 | 0 | 0 | 0 | 0 |
| | 96% | 0 | 0 | 0 | 0 | 0 | 0 | 0 | 0 | 0 | 0 |
| | 90% | 0 | 0 | 0 | 0 | 0 | 0 | 0 | 0 | 0 | 0 |
| | 80% | 0 | 0 | 0 | 0 | 0 | 1 | 0 | 0 | 0 | 0 |
| | 70% | 1 | 2 | 1 | 0 | 1 | 0 | 0 | 0 | 0 | 0 |
| | 60% | 1 | 2 | 2 | 1 | 1 | 0 | 1 | 0 | 0 | 0 |
| | 50% | 2 | 2 | 3 | 3 | 3 | 2 | 3 | 2 | 1 | 1 |
| | Untreated | 3 | 3 | 3 | 3 | 3 | 3 | 3 | 3 | 3 | 3 |
| Isopropanol | Undiluted | 0 | 0 | 0 | 0 | 0 | 0 | 0 | 0 | 0 | 0 |
| | 96% | 0 | 0 | 0 | 0 | 0 | 0 | 0 | 0 | 0 | 0 |
| | 90% | 0 | 1 | 0 | 0 | 0 | 0 | 0 | 0 | 0 | 0 |
| | 80% | 1 | 1 | 0 | 1 | 1 | 1 | 0 | 1 | 1 | 3 |
| | 70% | 2 | 2 | 1 | 1 | 1 | 0 | 1 | 1 | 0 | 2 |
| | 60% | 2 | 2 | 1 | 1 | 2 | 1 | 2 | 3 | 3 | 3 |

TABLE 14-continued

Reading of HSV - CPE after 44 hours with the detecting cell-layer.

| Alcohol | | 2 | | 4 | | 8 | | 16 | | 32 | |
|---|---|---|---|---|---|---|---|---|---|---|---|
| | 50% | 3 | 2 | 3 | 2 | 3 | 3 | 3 | 2 | 3 | 3 |
| | Untreated | 3 | 3 | 3 | 3 | 3 | 3 | 3 | 3 | 3 | 3 |
| Butanol | Undiluted | 0 | 0 | 0 | 0 | 0 | 0 | 0 | 0 | 0 | 0 |
| | 96% | 0 | 0 | 0 | 0 | 0 | 2 | 0 | 0 | 0 | 0 |
| | 90% | 0 | 0 | 0 | 1 | 0 | 0 | 1 | 0 | 0 | 3 |
| | 80% | 0 | 0 | 0 | 1 | 1 | 0 | 0 | 0 | 1 | 0 |
| | 70% | 0 | 0 | 0 | 1 | 1 | 0 | 0 | 1 | 1 | 1 |
| | 60% | 0 | 2 | 2 | 2 | 2 | 0 | 0 | 0 | 1 | 0 |
| | 50% | 0 | 2 | 2 | 2 | 2 | 2 | 0 | 0 | 1 | 0 |
| | Untreated | 3 | 3 | 3 | 3 | 3 | 3 | 3 | 3 | 3 | 3 |
| Ethanol | Undiluted | 0 | 0 | 0 | 0 | 0 | 0 | 0 | 0 | 0 | 0 |
| | 96% | 1 | 1 | 1 | 0 | 0 | 0 | 0 | 0 | 0 | 0 |
| | 90% | 1 | 1 | 1 | 0 | 0 | 0 | 0 | 0 | 0 | 0 |
| | 80% | 2 | 2 | 2 | 2 | 2 | 2 | 2 | 2 | 2 | 2 |
| | 70% | 3 | 3 | 3 | 3 | 3 | 3 | 3 | 3 | 3 | 3 |
| | 60% | 3 | 3 | 3 | 3 | 3 | 3 | 3 | 3 | 3 | 3 |
| | 50% | 3 | 3 | 3 | 3 | 3 | 3 | 3 | 3 | 3 | 3 |
| | Untreated | 3 | 3 | 3 | 3 | 3 | 3 | 3 | 3 | 3 | 3 |

(0: no CPE; 1, 2, 3: a few, several, all cells infected with HSV)

TABLE 15

% of virus-free wells in each row. (i.e. summing over time)

| Alcohol | Undiluted (99.9%) | 96% | 90% | 80% | 70% | 60% | 50% |
|---|---|---|---|---|---|---|---|
| Ethanol | 100% | 70% | 70% | 0% | 0% | 0% | 0% |
| Methanol | 100% | 80% | 60% | 40% | 10% | 20% | 10% |
| Propanol | 100% | 100% | 100% | 90% | 60% | 40% | 0% |
| Isopropanol | 100% | 100% | 90% | 20% | 20% | 0% | 0% |
| Butanol | 100% | 90% | 70% | 70% | 50% | 40% | 40% |

Conclusion: Ethanol, methanol, propanol, isopropanol, and butanol are all able to inactivate herpes simplex virus even intracellular virus.

Example 26

Mosquito Bites and Bee and Wasp Stings

Another batch of gel formed from the same types and amounts of components as in Example 24 was made up to test on bites and stings. As representative for insect bites, mosquito bites and Hymenoptera stings were investigated. Within the suborder of Hymenoptera, the apids, the stings of bee were examined while stings of wasp (yellow jacket type) were the representative within the suborder vespids.

The cases reported here are all accidental, all occurring in Europe.

Two types of investigations in accidental events were performed in the two representative indications, mosquito bites and bee/wasp stings:

a) One group of patients was directly treated and controlled by medical doctors.
b) Another group of patients was self-treated with the patients being themselves therapists, observers and reporters of activity.

Application Method and Dosage

As soon as possible after the sting or bite approximately 0.5 ml of the product is applied on the lesion point. Similar amount is reapplied if and when symptoms reoccur.

In relation to stings from the insect order Hymenoptera stingers embedded in the skin was scraped or brushed off with a blade or a fingernail before application.

26.1. Results of Treatment of Mosquito Bites 26.1.1 Treatments and Control by Medical Doctors Approximately 200 mosquito bites were treated. (Geographic distribution: Northern Europe: Denmark: Central Europe: South east, middle and South west of France).

In all patients the slight pain and especially the itching characterising the symptoms after a mosquito bite, disappeared almost spontaneously. Repeated applications within the following hour resulting in a complete disappearance of all pathological symptoms including swelling.

No side-effects were observed.

While the itching was the most frequent first symptom of a bite and while the direct bite itself was seldom noticed it is not possible to indicate an exact time from bite to treatment, and no direct diagnostic of mosquito type could be performed (all in central and northern Europe). With reference to the known time interval from mosquito bite to itching it is suggested that treatments were started within the first 5–10 minutes.

In a few cases treatments were started several hours or days after the bite. Also these patients reported a disappearance of itching and considerable diminution of oedematous reaction.

26.1.2 Patients' Self-treatment

In order to investigate the acceptance of efficacy under normal treatment conditions 30 patients received medication for self-treatment during a full summertime period. They all reported similar efficacy as reported under point 1.2.

There were no side effects.

Based on the reported comments it is presumed that this group altogether treated approximately 300–500 bites.

26.2. Results of Treatment of Bee and Wasp Stings 26.2.1 Treatments and Control by Medical Doctors Number of patients: 12 (Geographic distribution: Northern Europe: Denmark: Central Europe: South east, middle and South west of France).

Age group: 8–78 years of age. Average: 41 years.

Time from sting to treatment: Average 3.5 minutes, maximum 5 minutes.

Stinging insects: 1 bee, 11 wasps.

The severe distinct immediate pain following the sting disappeared within 1–3 minutes after the application. The local reaction, which immediately follows the sting was eliminated within 5–10 minutes. No wheal-and-flare reaction, no local edema and no swelling developed. The skin stayed normal apart from the distinct red spot indicating the physical penetration point of the stinger. No further reactions appeared in the following days of control.

26.2.2 Patients Self-treatment

Only 3 cases of from the self treating cases could with certainty be verified as wasp stings. The efficacy of the product in these cases were identical to the results reported under Example 26.2.1. No side-effects were reported.

26. Conclusion

The gelated concentrated ethanol has shown a very strong activity in mosquito bites and in bee and wasp stings.

We believe that the striking activity of the product is due to a direct inactivation of the venom, probably due to denaturation.

What is claimed is:

1. A method of treating skin affected by an outbreak of herpes, wherein an antiviral composition consisting essentially of more than 90% by weight alkanol selected from $C_{1-4}$ alkane-mono-ols, -diols and -triols and less than 10% water, is contacted with the area of skin affected by said outbreak and is retained in contact with said area for a period of at least about 1 hour.

2. A method according to claim 1 wherein a first dose of the said composition is retained in contact with said area for a first period of about 1 hour and then one or more further doses of said composition is (are) applied to and retained in contact with said area each for a further period of at least about 1 hour.

3. A method according to claim 2 wherein, following said further doses, one or more follow-up doses of said composition is (are) applied to and retained in contact with said area each for a period of about 3 to about 5 hours until said outbreak is cured.

4. A method according to claim 1 wherein the composition comprises an effective gelling amount of a polymeric gelling agent dissolved or dispersed in the alcohol.

5. A method according to claim 4 wherein the polymeric gelling agent has a molecular weight of at least about $10^4$ kDa and is present in the composition in an amount in the range 0.1 to 10% by weight.

6. A method according to claim 5 wherein the polymeric gelling agent is present in an amount in the range 0.5 to 2.0% by weight.

7. A method according to claim 1 wherein the said outbreak is of herpes labialis or herpes genitalis.

8. A method according to claim 1 wherein the composition is applied to and retained in contact with said area of skin from a cotton ball impregnated with said composition.

9. A method according to claim 1 wherein the concentration of alkanol in the composition is at least 95%.

10. A method according to claim 9 wherein said concentration is about 99%.

11. A method according to claim 2 wherein said first period is about 1 hour.

12. A method according to claim 2 wherein each said further period is about 1 hour and in which there are 2 to 4 said further periods.

13. A method according to claim 1 in which said alkanol is ethanol.

14. A method according to claim 8 in which said alkanol is ethanol.

15. A method of treating a skin eruption caused by an intracellular infection of herpes virus by applying to the infected tissue an antiviral composition consisting essentially of more than 90% by weight from $C_{1-4}$ alkane-mono-ols and -diols, and less than 10% by weight of water.

16. A method according to claim 15 which the alkanol is selected from methanol, ethanol, n-propanol, isopropanol, n-butanol and mixtures thereof.

17. A method according to claim 16 wherein the alkanol is selected from n-propanol and isopropanol and mixtures.

18. A method according to claim 16 in which the alkanol is n-propanol.

19. A method of treating a skin eruption caused by an intracellular infection of herpes virus by applying to the infected tissue a composition comprising at least 70% by weight n-propanol, and less than 30% by weight water.

20. A method of treating a skin eruption caused by an intracellular infection of herpes virus by applying to the infected tissue a composition comprising at least 80% by weight alkanol, selected from $C_3$- and $C_4$-alkane mono-ols and mixtures and less than 20% by weight water.

* * * * *